(12) United States Patent
Hogan

(10) Patent No.: US 8,146,836 B2
(45) Date of Patent: Apr. 3, 2012

(54) DEVICE FOR CARRYING AND DISPENSING SCENT

(76) Inventor: Jeffrey C. Hogan, Newman Lake, WA (US)

( * ) Notice: Subject to any disclaimer, the term of this patent is extended or adjusted under 35 U.S.C. 154(b) by 491 days.

(21) Appl. No.: 12/455,591

(22) Filed: Jun. 4, 2009

(65) Prior Publication Data
US 2010/0308131 A1 Dec. 9, 2010

(51) Int. Cl.
*A24F 25/00* (2006.01)
*A61L 9/04* (2006.01)

(52) U.S. Cl. ............. 239/36; 239/51.5; 239/53; 239/57; 239/60

(58) Field of Classification Search ............ 239/36, 239/51.5, 53, 57, 60, 34
See application file for complete search history.

(56) References Cited

U.S. PATENT DOCUMENTS

| | | | | |
|---|---|---|---|---|
| 3,784,102 A | * | 1/1974 | Stults | 239/36 |
| 4,735,010 A | * | 4/1988 | Grinarml | 43/1 |
| 7,121,475 B2 | * | 10/2006 | Thomas | 239/53 |

* cited by examiner

*Primary Examiner* — Dinh Nguyen

(57) ABSTRACT

A device for carrying and dispensing scent with a scent retaining block, a block retaining housing, a living hinge member, a housing cover plate, a latch member, right and left housing strap apertures, an adjustable length strap attached by male and female strap retaining members. The housing is rectangular and has one fully open portion. The housing cover plate is attached to the housing by the living hinge member. The housing has a plurality of apertures allowing air to freely pass into and out of the housing. The adjustable strap is attached to the left strap aperture. The non adjustable strap is attached to the right strap aperture or vice versa. The adjustable strap is removably attached to the non adjustable strap by the male and the female strap retaining members. The scent block is constructed from an absorbent material capable of retaining a liquid scent without leaking.

6 Claims, 5 Drawing Sheets

DEVICE FOR CARRYING AND DISPENSING SCENT

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of hunting accessories and more specifically to a device for carrying and dispensing scent.

Many of the commercially available scented substances are provided in liquid form and applied directly to the clothes or boots of the hunter. The scent, however, ordinarily wears off relatively quickly because of the type of fabrics commonly used for hunting apparel. This tenancy is exacerbated by rain and other conditions that cause the scent to be rubbed off or diluted.

Various types of devices have attempted to solve the stated problems. For example, devices have been designed that involve wrist bands or leg bands that have the ability to absorb liquid scent and to be worn on the user.

However there is a deficiency in the prior technology in that the existing products do not let the user easily remove and replace the scented component. Another deficiency is that the existing products do not have ample flexibility to allow the device to be attached on the relatively small diameter of a user's wrist or arm or to the relatively large diameter of a person's thigh or the trunk of a tree. Finally, existing products do not have a superior liquid retaining member that can absorb a relatively large amount of liquid without the leakage problems that are associated with many liquid retaining members currently in use.

BRIEF SUMMARY OF THE INVENTION

The primary object of the invention is to provide a device for carrying and distributing scent that can be easily replenished with a removable and replaceable scent retaining block.

Another object of the invention is to provide a device for carrying and distributing scent that can be securely attached to items of varying diameters.

Another object of the invention is to provide a device for carrying and distributing scent that allows for the user to easily switch scent carrying blocks from one type to another.

A further object of the invention is to provide a device for carrying and distributing scent where the scent retaining block is absorbent but does not leak excess fluid.

Other objects and advantages of the present invention will become apparent from the following descriptions, taken in connection with the accompanying drawings, wherein, by way of illustration and example, an embodiment of the present invention is disclosed.

In accordance with a preferred embodiment of the invention, there is disclosed a device for carrying and dispensing scent comprising: a scent retaining block, a block retaining housing, a living hinge member, a housing cover plate, a latch member, a right housing strap aperture, a left housing strap aperture, an adjustable length strap, a male strap retaining closure, a female strap retaining closure, a non adjustable strap member, said housing being generally rectangular and having one open portion, said housing cover plate attached to said housing by said living hinge member, said cover plate removably retained to said housing by said latch member, said housing having a plurality of apertures allowing air to freely pass through into and out of said housing, said adjustable strap fixedly attached to said left strap aperture, said non adjustable strap fixedly attached to said right strap aperture, said adjustable strap removably attached to said non adjustable strap by said male and said female strap retaining members, and said block being constructed from an absorbent material capable of retaining a liquid scent without leaking.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
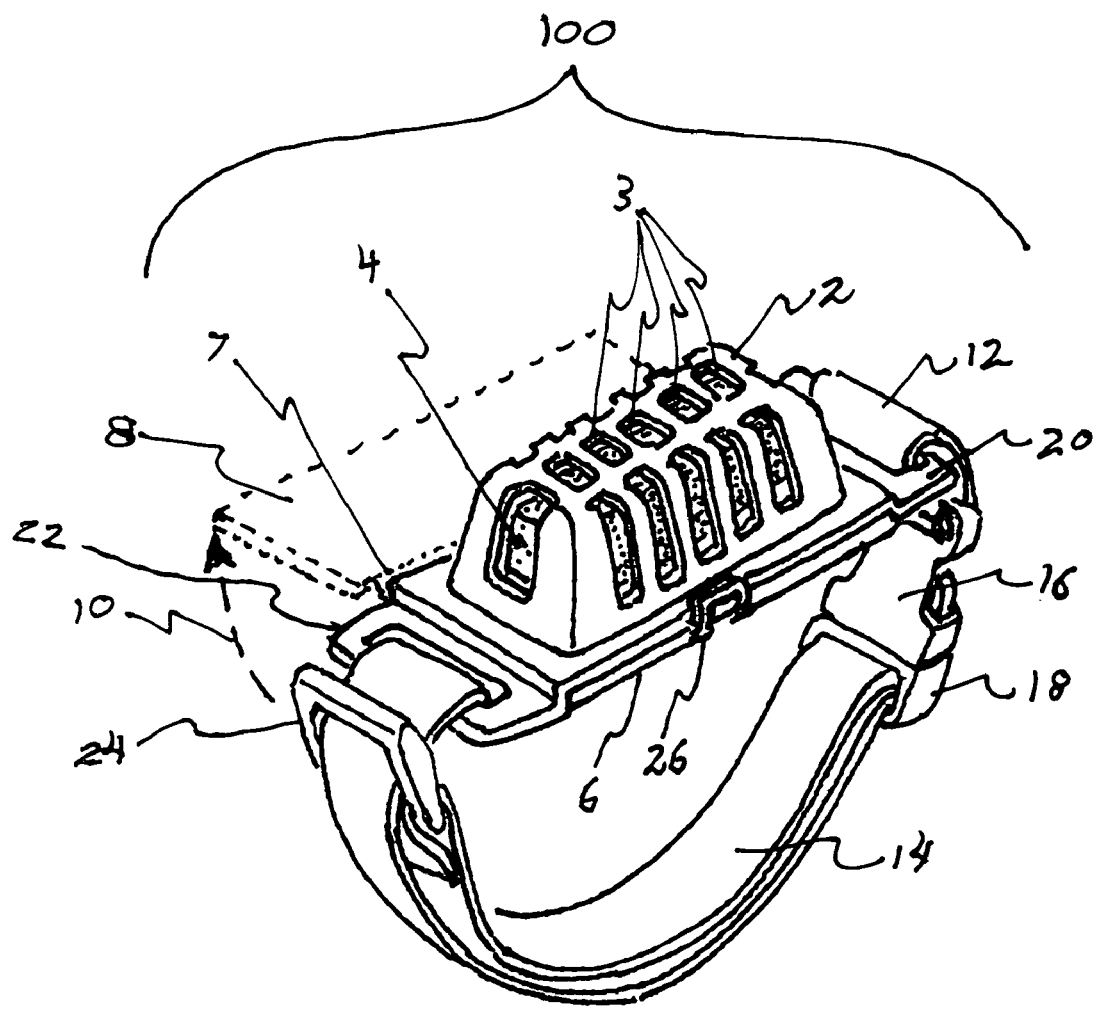
FIG. 1 is a perspective view of the invention.

Referring now to FIG. 1 we see a perspective view of the invention 100. A rigid housing 2 is made of injection molded plastic and includes a plurality of vent apertures 3 that let scent that is stored in liquid absorbing block 4 to exit the housing 2 in a relatively unimpeded manner. The housing 2 is open on its bottom. The bottom open portion is covered by housing cover plate 6 and retained by living hinge 7 on one side an housing latch 26 on the opposite side. The preferred plastic used in housing 2 is high density polypropylene because of its ideal living hinge capability. The housing cover 6 can be shown in the swung open position represented by dotted lines 8 and swing line 10. The housing 2 includes a left 22 and right 20 flange. Each flange 20, 22 includes an aperture that allows a standard strap member to be attached. Because the swinging housing cover 6 is on the underside of housing 2, there is little chance of the cover 6 being accidentally opened because it is trapped between the flanged, secured housing and the wearer's arm or leg. A fixed length strap 16 is attached to the right flange aperture 20 and an adjustable length strap 14 is attached to an aperture in the left flange 22. Obviously, the left and right orientation of straps can be reversed where the fixed strap is attached to the left flange 20 and the adjustable strap can be attached to the right flange 22.

Figure 2:
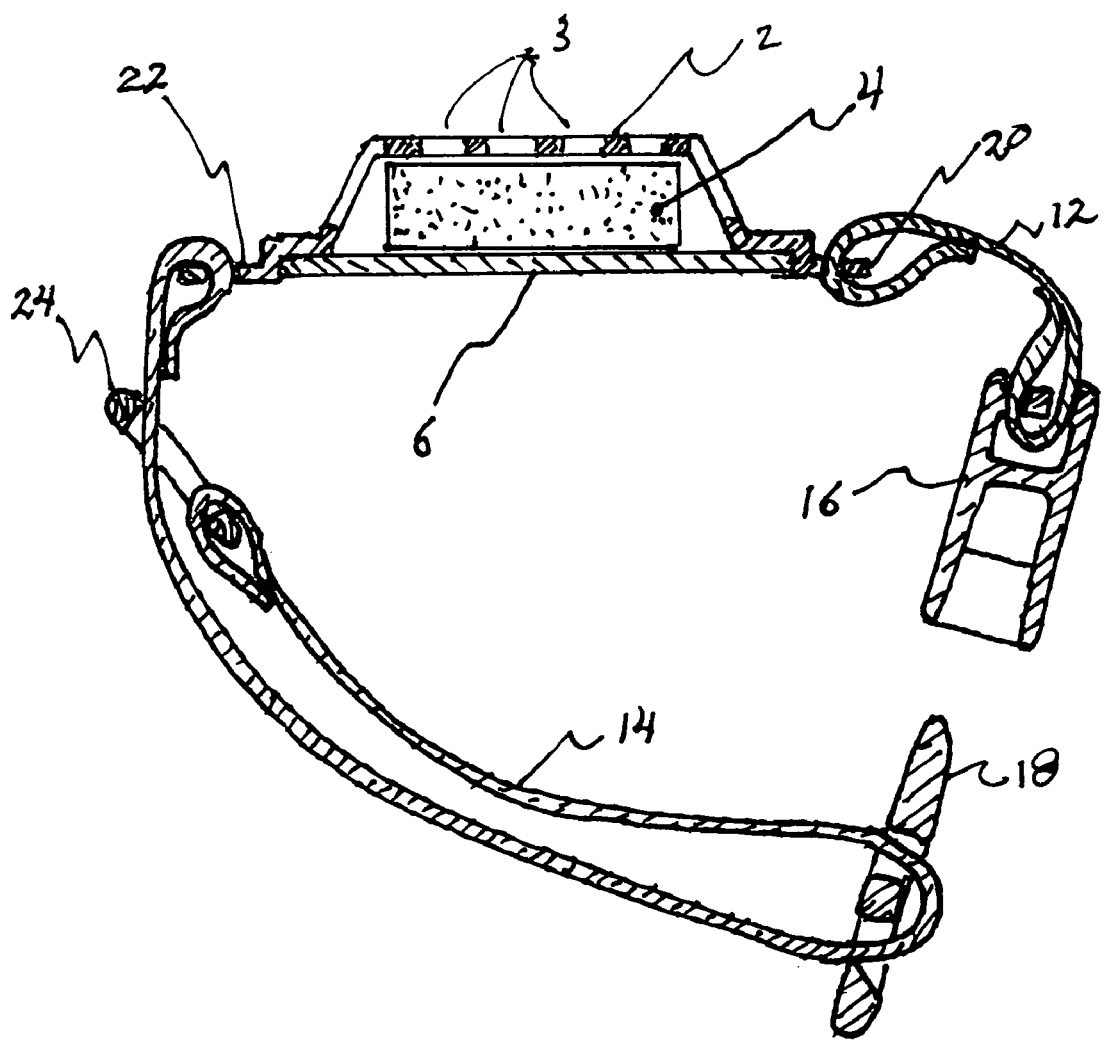
FIG. 2 is a side section view of the invention.

FIG. 2 shows a side section view of the invention that bisects the entire invention 100. Scent absorbing block 4 can be clearly seen residing inside housing 2. The absorbent, scent releasing block is easily removable and replaceable. This allows the user to remove the block and store it in a sealed storage container and to replace the block 4 with one that may create a different scent. The user may choose a scent block that lures an animal such as a deer. The user may then decide to remove that block and replace it with a scent block that masks the presence of a hunter when in close proximity to a game animal. Still another block may be used to repel flying insects such as mosquitoes. The block 4 is approximately one half inch wide, one half inch tall and one and one half inches long. It is constructed of one hundred percent polyester fiber that has been manufactured by a needle punch construction. Fixed strap 12 can be clearly seen attached to left flange 20 and terminating at its opposite side in a standard female strap retaining closure member 16. An adjustable length strap 14 is fixedly attached at one end to flange 22. The adjustable length strap 1 is threaded through an aperture in male strap retaining closure 18 and terminates in a sliding strap clip 24. The clip 24 can be slid down thereby effectively making longer the usable length of the strap member 14. In this way, the user can adjust the diameter of the strap from approximately three and one half inches to a maximum of approximately seven inches.

Figure 3:
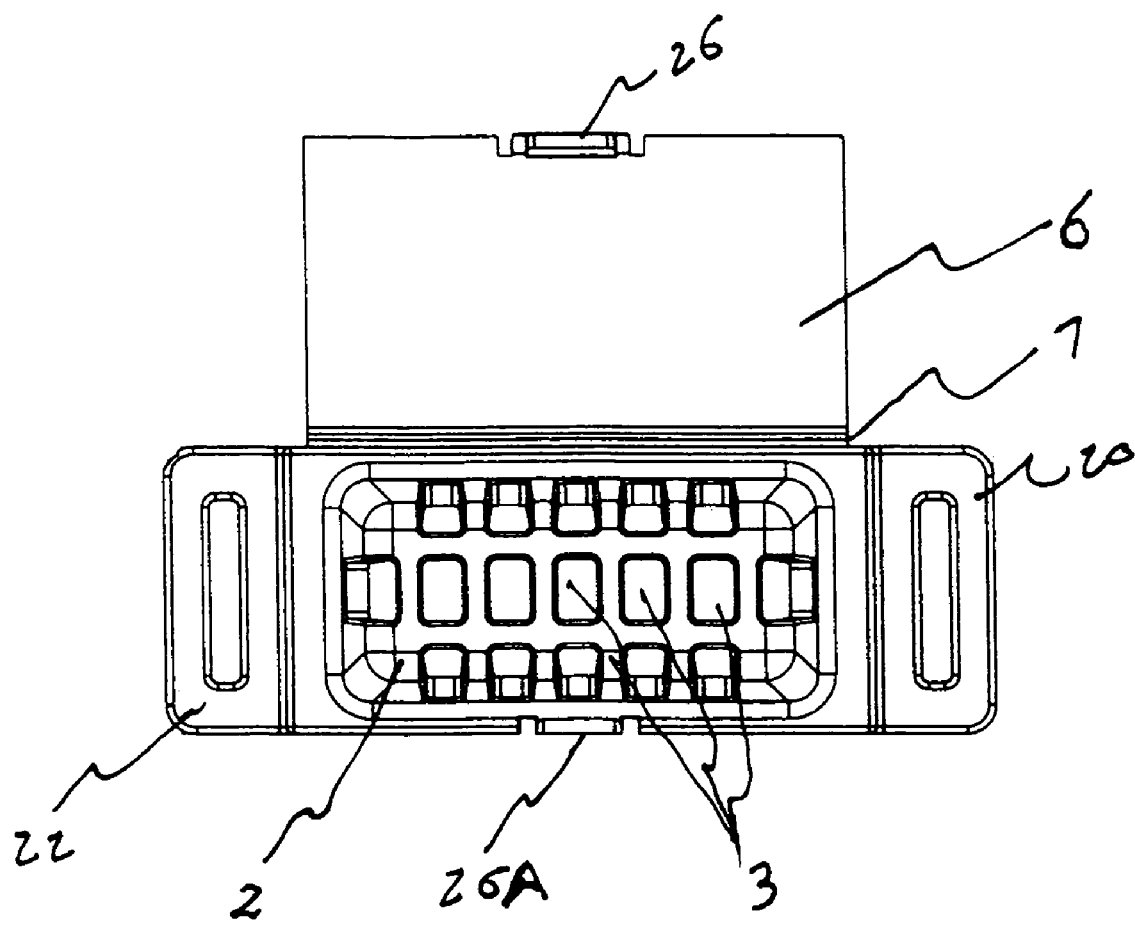
FIG. 3 is a top plan view of the housing of the invention.

FIG. 3 shows a top plan view of the housing portion 2 of the invention. Flanges 20, 22 can be clearly seen. The housing cover plate 6 is shown in the folded open position. Living hinge 7 can also be clearly seen. The many apertures 3 allow the scent contained in block 4 to flow out in an unimpeded fashion. Housing cover plate latch 26, and mating latch flange 26A can be clearly seen.

Figure 4:
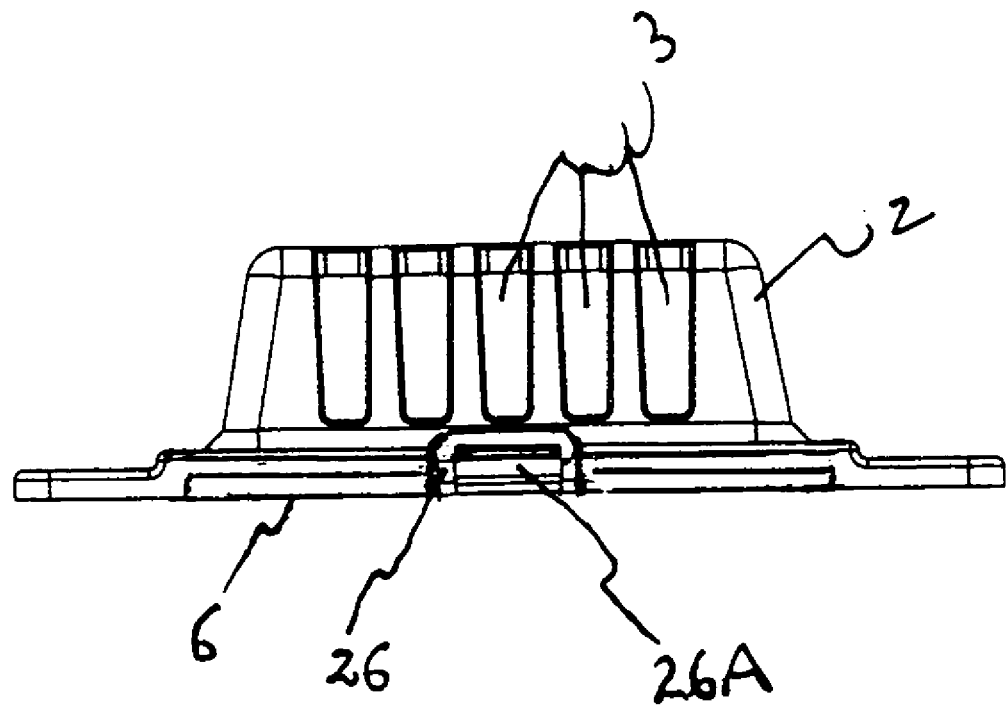
FIG. 4 is a side view of the housing of the invention.

FIG. 4 shows a side view of the housing 2 of the present invention. Latch 26 can be clearly seen and is engaged to latch flange 26A.

Figure 5:
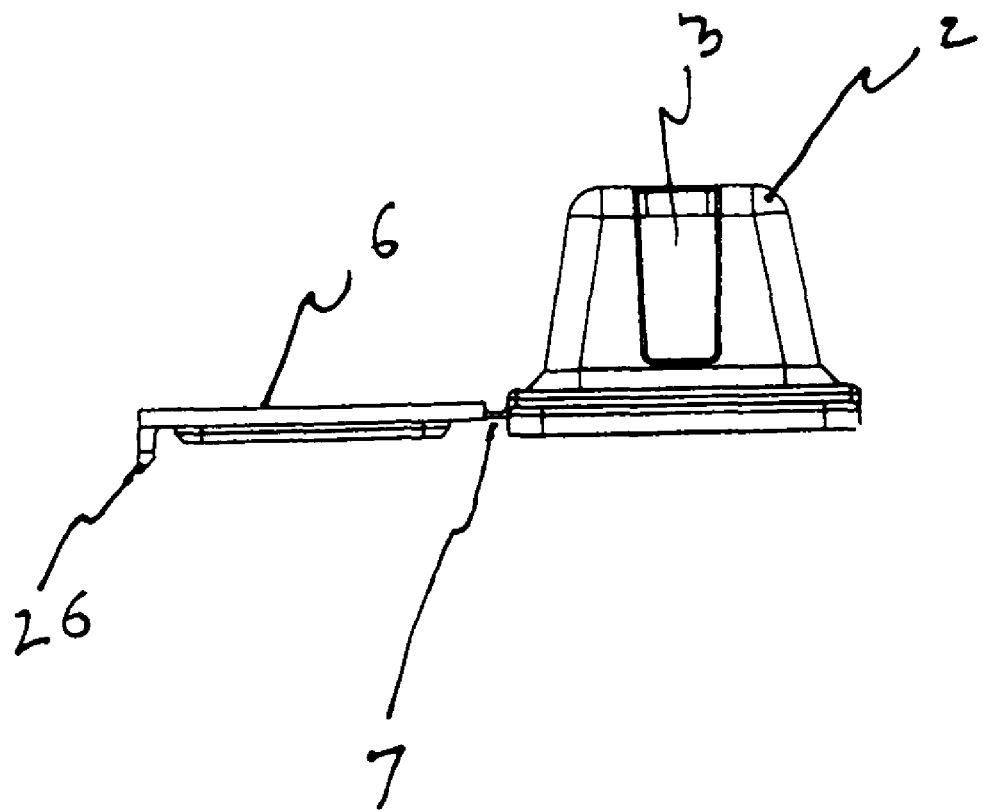
FIG. 5 is an end view of the housing of the invention.

FIG. 5 is shows an end view of the housing 2 of the present invention. Living hinge 7 is clearly seen, as well as latch member 26.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. device for carrying and dispensing scent comprising:
a scent retaining block;
a block retaining housing;
a living hinge member;
a housing cover plate;
a latch member;
a right housing strap aperture;
a left housing strap aperture;
an adjustable length strap;
a male strap retaining closure;
a female strap retaining closure;
a non adjustable strap member;
said housing being generally rectangular and having one open portion;
said housing cover plate attached to said housing by said living hinge member;
said cover plate removably retained to said housing by said latch member;
said housing having a plurality of apertures allowing air to freely pass into and out of said housing;
said adjustable strap fixedly attached to said left strap aperture;
said non adjustable strap fixedly attached to said right strap aperture;
said adjustable strap removably attached to said non adjustable strap by said male and said female strap retaining members; and
said block being constructed from an absorbent material capable of retaining a liquid scent without leaking.

2. Device for carrying and dispensing scent as claimed in claim 1 wherein said scent retaining block is constructed of polyester fibers made by a needle punch process.

3. Device for carrying and dispensing scent as claimed in claim 1 wherein said housing and housing cover and said living hinge are constructed of injection molded polypropylene.

4. Device for carrying and dispensing scent as claimed in claim 1 wherein said scent retaining block is approximately one half of an inch wide, one half of an inch tall and one and one half of an inch long.

5. Device for carrying and dispensing scent as claimed in claim 1 wherein said adjustable strap can be adjusted between three and one half inches in diameter to seven inches in diameter.

6. Device for carrying and dispensing scent as claimed in claim 1 wherein said housing cover is located on the underside of said housing thereby trapping said cover between said housing and the arm or leg of the wearer.

* * * * *